United States Patent [19]
Giovanoni

[11] Patent Number: 5,575,995
[45] Date of Patent: Nov. 19, 1996

[54] FERRIC SUBSULFATE GEL AND METHODS OF USING SAME

[76] Inventor: Richard L. Giovanoni, 155 Webster St., Hanover, Mass. 02339

[21] Appl. No.: 470,132

[22] Filed: Jun. 6, 1995

Related U.S. Application Data

[63] Continuation of Ser. No. 314,747, Sep. 29, 1994, abandoned, which is a continuation of Ser. No. 745,195, Aug. 15, 1991, abandoned.

[51] Int. Cl.$^6$ ............................ A61K 33/26; A61L 25/00
[52] U.S. Cl. .................................. 424/78.06; 424/78.24; 424/647; 514/944; 602/904
[58] Field of Search ...................... 424/78.24, 401, 424/647, 78.06; 514/827, 828, 944; 602/904

[56] References Cited

U.S. PATENT DOCUMENTS

| | | | |
|---|---|---|---|
| 4,617,950 | 10/1986 | Porteous et al. | 132/91 |
| 5,011,693 | 4/1991 | Whitefield | 424/455 |
| 5,021,053 | 6/1991 | Barclay et al. | 604/892.1 |
| 5,140,016 | 8/1992 | Goldberg et al. | 514/57 |
| 5,143,724 | 9/1992 | Leschiner et al. | 424/78.08 |

*Primary Examiner*—Melvyn I. Marquis
*Assistant Examiner*—Robert H. Harrison
*Attorney, Agent, or Firm*—Vorys, Sater, Seymour & Pease

[57] ABSTRACT

Lesions surgically or otherwise induced on living tissue are treated by applying to the tissue a gel containing a water solution of ferric subsulfate, glycerin to thicken the solution and polyvinyl pyrrolidone as a film forming material.

13 Claims, No Drawings

FERRIC SUBSULFATE GEL AND METHODS OF USING SAME

This is a continuation of application Ser. No. 08/314,747 filed on Sep. 29, 1994, abandoned, which is a continuation of application Ser. No. 07/745,195, filed on Aug. 15, 1991, abandoned.

FIELD OF THE INVENTION

The present invention relates generally to astringent and styptic compositions, and more specifically to a form of Monsel's Solution that is utilized both for those properties and for effective hemostasis following surgical procedures.

BACKGROUND OF THE INVENTION

A solution of ferric subsulfate has been recognized as a medicament used for its astringent/styptic properties since at least as early as 1960 when it was listed in National Formulary XI. It has been listed there and in subsequent editions as ferric subsulfate solution or Monsel's Solution or basic ferric sulfate solution. It is there identified as a reddish-brown liquid, nearly odorless, with a sour, strongly astringent taste. It is acid to litmus, is affected by light, and has a specific gravity of about 1.548. As referenced in Remington's *Practice of Pharmacy*, 13th ed., ferric subsulfate solution is stated to be prepared by the oxidation of ferric sulfate nitric acid. It is an important styptic solution because it is less irritating than ferric sulfate because of the lesser amount of sulfuric acid present.

In practice, a ferric subsulfate solution is prepared by the oxidation of ferrous ferric sulfate with nitric and sulfuric acids. Listed below is an equation that is believed to approximate that used to form ferric subsulfate.

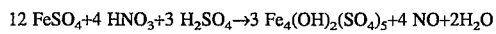

$$12\ FeSO_4 + 4\ HNO_3 + 3\ H_2SO_4 \rightarrow 3\ Fe_4(OH)_2(SO_4)_5 + 4\ NO + 2H_2O$$

When maintained in aqueous solution, ferric subsulfate presents definite problems of usage. Ferric subsulfate is miscible with water. As a consequence, the reacted solution may also contain remnants of the nitric and sulfuric acids used to form the compound, and it will be apparent that any excess nitric and/or sulfuric acid in the solution will greatly enhance the skin irritating characteristics of the solution. Additionally, the solution sporadically crystallizes and precipitates at room temperature, which characteristic is enhanced at temperatures below room temperature. Even upon redissolving of the precipitated or crystallized subsulfate by heating, the official solution is murky rather than clear; so, it is difficult to determine whether the crystallized or precipitated ferric subsulfate has been completely dissolved or merely dispersed in the aqueous medium. Indeed, as marketed, e.g., by Spectrum Mfg. Co., of Gardena, Calif., there is a notation that the product may crystallize.

As a consequence, it is difficult without titrating the solution to determine whether a ferric subsulfate solution is of the proper strength. Such an assay is described in *National Formulary* XI, titration being carried out against sodium thiosulfate after the addition of HCl and KI. The official solution contains 20 to 22 grams of iron per 100 ml. Thus, it would be advantageous to utilize a form of ferric subsulfate which requires a lesser concentration of the active ingredient, thereby mitigating adverse side effects caused by the ferric subsulfate.

It is, therefore, a primary object of the present invention to provide a ferric subsulfate composition that has substantially the same astringent and styptic properties of Monsel's Solution, but is less irritating than Monsel's Solution to the skin, mucous membrane, and other target tissue.

It is another object of the present invention to provide a ferric subsulfate astringent in a form in which the amount of iron-containing subsulfate may be accurately maintained and applied to target tissues, and in which the concentration of iron is substantially less than the 20 to 22% iron of Monsel's Solution.

It is still another object to provide ferric subsulfate in a form in which it can be assured that there is a substantial absence of the nitric and sulfuric acids used to prepare the subsulfate.

SUMMARY OF THE INVENTION

In composition form, the present invention comprises a water solution of ferric subsulfate, a thickening agent in which the ferric subsulfate is soluble in order to thicken the subsulfate solution to a desired viscosity, and a film forming material in an amount sufficient to form a gel such that, when applied to target tissue, the gel will have an iron concentration substantially less than the 20 to 22% iron present in officially recognized Monsel's Solution. In gel form, the ferric subsulfate solution can be easily applied to target tissue and has been determined to have far less irritating characteristics than Monsel's Solution. More specifically, the ferric subsulfate gel of the present invention contains 2 to 6% iron, most preferably 3% iron. The thickening agent for the solution is most preferably glycerin, and the preferred film former is polyvinyl pyrrolidone.

Although the composition with the film forming material is most preferred at present, it is also desired to be included within the scope of my invention a composition that does not include a film former. This composition primarily contains ferric subsulfate and a thickener, e.g., glycerin, in which the subsulfate is soluble. Preferred concentrations of active material are about 24 to 50 percent ferric subsulfate, and about 2 to 6 percent iron.

For utility, the subject composition is used to treat lesions by applying the gel to target tissue. It is also used to provide hemostasis in conjunction with cervical and general surgical procedures.

These and other objects, features and advantages of the present invention will be more readily understood when considered in conjunction with a preferred embodiment of the invention as described hereinafter.

DETAILED DESCRIPTION OF BEST MODE

For the best mode of my invention I prefer to use ferric subsulfate, a thickening agent, a film forming or gelling agent, and an antibacterial or preservative, together with water.

The ferric subsulfate is preferably supplied in the form of a purified powder, so that no substantial quantities of residual nitric acid or sulfuric acid are present, which is often the case with Monsel's Solution. Utilizing a purified powder and then dissolving it in water will alleviate much of the irritation caused by those acids. The ferric subsulfate is not only dissolved in the aqueous portion of the present composition, but, where desired, a thickening agent is used so that the gel that will subsequently be formed has additional body and a more gel-like structure.

In forming the gel of the present invention, I have found it most desirable to use glycerin as the thickening agent, because it not only increases the viscosity of the gel but the ferric subsulfate is soluble in glycerin. Thus, the glycerin serves a dual function of not only being a viscosity agent but also solubilizer for the subsulfate. Because of that characteristic, the gel is rendered clear and substantially translucent, and thus has a superior aesthetic effect than if the viscosity agent were not a solubilizer for the ferric subsulfate, in which case a suspension would be formed with a far greater degree of opacity. Thus, while glycerin is the preferred viscosity agent, other materials may be utilized for that function although, if they are not solubilizing agents for the subsulfate, they will not be as cosmetically appealing, i.e, they will not form a relatively clear gel.

The preferred film former is polyvinyl pyrrolidone ("PVP"). When used in convenient quantities, the PVP, together with the glycerin, will provide a thick gel vehicle that is easily utilized. PVP is the preferred film former or gelling agent, particularly because it is not readily susceptible to microbial contamination and therefore does not require large amounts of potentially irritating antimicrobial agents. However, other gel formers may be used. For example, it would be possible to use pectin, a mucilagenous material obtained from citrus fruits, Carbopol, a semisynthetic polymer composed of acrylic acid crosslinked with allyl sucrose; sodium alginate, a highly polymerized dextromannuronic acid anhydride obtained from seaweed, or even some finely divided clays such as bentonite. Since, PVP is well established for medical use and tends to create a "chemical bandage" over the surgically induced crater that may be formed in the cervix wall, it has a clinical advantage and stays in contact with the target tissue for an extended period of time, thus physically protecting the traumatized tissue and allowing prolonged availability of the drug to the target tissue. Thus, PVP, because of its long-term documented safety in humans and other advantages, is the preferred film-former.

Other materials are utilized in my preferred composition. For convenience, purified water is present in order to adjust the viscosity of the gel, in addition to glycerin. It is also advisable to use a preservative, i.e., an anti-bacterial agent, and at present benzalkonium chloride is preferred, although it will be apparent that other preservatives can be substituted. For example, other preservatives such potassium sorbate, sorbic acid, thimerosal and chlorhexidine might also be used in place of benzalkonium chloride.

With respect to the quantities of the various ingredients, the quantities to be utilized are those required to achieve the desired gel characteristics. For example, the more body or substance the gel will have, the more PVP or gelling agent will be used. The thicker the gel desired, the greater the amount of viscosity agent, e.g., glycerin, will be utilized. However, it has been found that concentrations of 20–25% PVP and 10–15% glycerin in the final gel are preferred.

Will respect to the quantities of ferric subsulfate, approximately 25% of the gel has been found to be an effective amount, with a range of perhaps 24–50% being considered preferred. That amount of ferric subsulfate generally provides a gel which contains 2–6% iron per 100 ml. of the gel, which has been found to be an amount that will have an effect substantially equivalent to that of the Monsel's Solution. Lesser concentrations, e.g., 24 to 28% subsulfate and 2–4% iron are more preferred in a composition including a film-former. The pH of the gel is approximately 2.3 to 3.3, with a pH of about 2.8 being most preferred. Thus, the most preferred formulation that constitutes the presently known, best mode of my invention, is as follows:

| Polyvinyl Pyrrolidone K-30 | 23.2% |
| Glycerin USP | 13.3% |
| Benzalkonium Chloride | 0.005% |
| Ferric Subsulfate | 25.9% |
| Water, Purified | 37.6% |

In manufacturing the gel from the above formula, the benzalkonium chloride and glycerin are dissolved in the formula amount of water while being heated to approximately 40° C. to form an aqueous solution. Approximately 70% of that solution is mixed with the formula amount of PVP K-30 using constant stirring, and after the PVP has been totally hydrated, the pH of the mixture is determined. Allowable limits are a pH of 4.0 to 5.0. Thereafter, the formula amount of powdered ferric subsulfate is slowly added together with the remainder the aqueous solution of preservative, glycerin and water. Stirring is maintained until the mass exhibits a uniform, dark brown color. The mass is allowed to stand until an aliquot exhibits clarity and the dark brown color is uniform throughout the product mass. The pH should now be between 2.3 and 3.3. Thereafter, the bulk is filled into glass, amber-colored containers and sealed.

When viewed in a broader sense, the composition of my invention can also consist of a similar formula to the preferred embodiment, but without the presence of a film-former, i.e., polyvinyl pyrrolidone. In such a composition the gel will still have the visco-tenacious properties of the PVP formula, but will not act as a "chemical bandage," a characteristic it possesses with the inclusion of PVP.

Without the film-former the ferric subsulfate will be present in greater concentrations, viz., toward the upper end of 24 to 50% by weight, and the iron concentration will be at least in the middle of a 2 to 6% range. Without PVP preferred amounts of ferric subsulfate and iron are about 31.1% and 3.6%, respectively. Thus, the best mode of my invention without a film-former is:

| Ferric Subsulfate | 31.1% |
| Glycerin USP | 68.7% |
| Benzalkonium Chloride | 0.005% |
| Water, Purified | 0.195% |

In application, the gel is applied directly to an area that has been subjected to trauma. It may be applied to a lesion to coat same or to an area, especially the cervix, which has been subjected to a surgical procedure, perhaps immediately after or during same. In this manner the gel of the present invention coats and, being water soluble, infiltrates the target tissue that has been subjected to trauma and, by virtue of its astringent/styptic properties, acts to prevent bleeding. Lasting hemostasis at the area of the target tissue is achieved, as well as the provision of a film that coats the target tissue and protects it from air or body fluid-born bacteria.

Compared with Monsel's Solution, the gel contains 14% of the iron concentration of Monsel's Solution but, based on present information, performs in a manner clinically equivalent to Monsel's Solution. As a consequence, far less drug is needed to effect the same clinical end result—lasting hemostasis. Thus, the gel dosage form insures stability and solubility of the active drug with less irritancy than that provided by Monsel's Solution, even if all of the nitric acid and sulfuric acid used to prepare the Monsel's Solution are certain to have been removed prior to use. Further, because the gel creates a chemical bandage over, e.g., a surgically induced crater formed in the cervix wall, that physical barrier tends to retard the washing away of the drug and allows it to stay in contact with the target tissue for an extended period of time, thereby physically protecting the target tissue and allowing prolonged availability of the drug to that tissue. When the term, gel, is used herein, it is used in a broad sense to include a semisolid substance having a somewhat greater consistency than a sol. The term, gel, is intended to represent the physical, gelatinous characteristic of the material rather than being limited to a restrictive, technical definition of a colloidal suspension of a solid in a liquid, since, as will be apparent, the ferric subsulfate of the subject gel is dissolved in the water and glycerin rather than being suspended in it.

It will be apparent to those of skill in this art that various alterations and modifications may be made in the best mode of my invention described hereinbefore without departing from the purview of that invention. A wide range of viscosity agents and gelling agents or film formers may be utilized although the agents set forth in that best mode appear at present to be clearly superior. As a consequence, I desire that the present invention not be limited by that best mode but be deemed to have a scope as defined by the following, appended claims, including equivalents thereof.

I claim:

1. A method of treating lesions on surgically or otherwise traumatized tissue, which comprises applying to such tissue a gel containing a water solution of ferric subsulfate, glycerin as a thickening agent in which said ferric subsulfate is soluble in an amount sufficient to thicken the solution, and polyvinyl pyrrolidone as a film forming material in an amount sufficient to create a gel-like structure such that when removed from a container the gel tends to retain its shape, and in which the iron concentration is substantially less than the 20 to 22% iron present in officially recognized Monsel's solution.

2. A method as claimed in claim 1, in which the pH of said gel is about 2.3 to 3.3.

3. A method of claimed in claim 1, in which the pH of said gel is about 2.8.

4. A method as claimed in claim 1, in which said lesions are treated in conjunction with cervical surgical procedures performed on said target tissue.

5. A method as claimed in claim 4, in which said lesions are treated during said cervical surgical procedures.

6. A method as claimed in claim 4, in which lesions are treated after said cervical surgical procedures.

7. A method as claimed in claim 1, in which said lesions are treated to provide hemostasis.

8. A method as claimed in claim 4, in which the iron concentration is about 2 to 6 grams per ml.

9. A method as claimed in claim 1, in which the iron concentration is about 3 grams per ml.

10. The method of claim 1 wherein said glycerin is present in said water solution of ferric subsulfate in a concentration of 10–15% by weight.

11. The method of claim 10 wherein said glycerin is present in said water solution of ferric subsulfate in a concentration of about 13.3% by weight.

12. The method of claim 1 wherein said polyvinyl pyrrolidone is present in said water solution of ferric subsulfate in a concentration of 20–25% by weight.

13. The method of claim 10 wherein said polyvinyl pyrrolidone is present in said water solution of ferric subsulfate in a concentration of about 23.2% by weight.

* * * * *